(12) United States Patent
Narkhede (10) Patent No.: US 11,253,284 B2
(45) Date of Patent: Feb. 22, 2022

(54) INSTRUMENT WITH A DETACHABLE MOTOR DRIVE ASSEMBLY, TELESCOPE AND CUTTER TUBE ASSEMBLY

(71) Applicant: XCELLANCE MEDICAL TECHNOLOGIES PVT.LTD, Navi Mumbai (IN)

(72) Inventor: Pradip Barsu Narkhede, Navi Mumbai (IN)

(73) Assignee: XCELLANCE MEDICAL TECHNOLOGIES PVT. LTD, Navi Mumbai (IN)

( * ) Notice: Subject to any disclaimer, the term of this patent is extended or adjusted under 35 U.S.C. 154(b) by 126 days.

(21) Appl. No.: 16/464,420

(22) PCT Filed: Dec. 10, 2017

(86) PCT No.: PCT/IN2017/050584
§ 371 (c)(1),
(2) Date: May 28, 2019

(87) PCT Pub. No.: WO2018/109783
PCT Pub. Date: Jun. 21, 2018

(65) Prior Publication Data
US 2021/0113233 A1 Apr. 22, 2021

(30) Foreign Application Priority Data
Dec. 14, 2016 (IN) .............................. 201621042633

(51) Int. Cl.
*A61B 17/32* (2006.01)
*A61B 90/00* (2016.01)
*A61B 17/00* (2006.01)

(52) U.S. Cl.
CPC ................... *A61B 17/32002* (2013.01); *A61B 2017/0046* (2013.01); *A61B 2017/00274* (2013.01); *A61B 2017/320024* (2013.01); *A61B 2090/0813* (2016.02)

(58) Field of Classification Search
CPC .............. A61B 17/32002; A61B 2017/320024
See application file for complete search history.

(56) References Cited

U.S. PATENT DOCUMENTS

| 8,100,928 | B2 * | 1/2012 | Nohilly | .......... | A61B 17/320758 606/180 |
| 2013/0324882 | A1 * | 12/2013 | Mescher | ............ | A61B 10/0283 600/566 |
| 2015/0305772 | A1 * | 10/2015 | McCauley | ......... | A61B 17/3423 606/114 |

* cited by examiner

*Primary Examiner* — Sarah A Simpson
(74) *Attorney, Agent, or Firm* — Taft Stettinius & Hollister LLP; Derek B. Lavender (57) ABSTRACT

An instrument with a motor drive assembly detachable from a handle assembly and detachable from a gear assembly, where the gear assembly is inside the handle assembly and further the instrument comprising a standard telescope which is detachable from the instrument and a cutter/blade assembly detachable from an outer sheath. In an aspect, an instrument (1) includes a motor drive assembly (2) that is detachable from a handle assembly (3) and detachable from a gear assembly (5), wherein the gear assembly (5) is positioned inside the handle assembly (3), and wherein the motor drive assembly (2) is detachable for the purpose of being reused after cleaning or its replacement.

7 Claims, 11 Drawing Sheets

SECTION A-A

SECTION B-B

INSTRUMENT WITH A DETACHABLE MOTOR DRIVE ASSEMBLY, TELESCOPE AND CUTTER TUBE ASSEMBLY

FIELD OF THE INVENTION

The present invention relates, in general, to an instrument and more particularly, to a medical instrument comprising of a motor drive assembly detachable from a handle assembly and detachable from a gear assembly. The gear assembly of the medical instrument is inside the handle assembly and further the medical instrument includes a standard telescope which is detachable from the instrument and a cutter/blade assembly detachable from an outer sheath. Further, outer sheath can be detached from handle assembly.

BACKGROUND OF THE INVENTION

Till date various medical instruments have been used in urological surgeries with an inbuilt motor assembly and a telescope in it. Various urological surgeries, such as transurethral surgery, for treating a benign prostatic hyperplasia (BPH) includes removal of the excess prostatic tissue.

Surgeons use these and other available instruments during the urological surgeries to morcellate a tissue into smaller pieces. At the end of the surgery/operation, these pieces of excised prostatic tissue are flushed out of a bladder using irrigation, and are aspirated out using a large bore syringe, and/or removed through a resectoscope using a grasping device.

However, due to an inbuilt motor assembly, it is observed that such instruments have to be replaced completely along with the motor assembly after several uses. Also, a blade assembly in such medical instruments wears after using it for number of times. Further, a cleaning of the internal parts of such instruments is very cumbersome as the internal parts are generally not separable or detachable. Furthermore, in existing medical devices the telescope is fixed, hence if such telescope gets damaged the whole device needs to be replaced.

Thus, in view of the above and other existing issues in the medical instruments used in urological surgeries, there is a direct need to provide a new instrument that has a motor assembly that is detachable from the handle assembly and also detachable from the gear assembly. Further, the motor assembly after detachment should be capable of being cleaned and/or sterilized and/or autoclaved and reused or replaced completely if it wears after multiple uses, thereby reusing the handle assembly and the gear assembly with a new motor assembly making it user friendly and cost effective.

The instrument shall also allow cleaning and/or sterilizing and/or autoclaving of the handle assembly and/or the gear assembly after the motor assembly is detached.

Furthermore, there is also a need for a cutter tube that can be detached from an outer tube of the instrument for cleaning and/or sterilizing and/or autoclaving and reusing it or replace it with a new one when it wears after multiple uses.

It may be appreciated that, there are instruments available in prior-art that includes a telescope at various angles to the instrument for viewing the surgery which adds complexity in the optic mechanism.

Thus, there is further a need of a telescope which is detachable from the instrument for reusing it after cleaning and/or sterilizing and/or autoclaving it or replace it with a new standard telescope such that the telescope is attached in a straight alignment to the cutter tube of the instrument that allows for detachment in a straight angle rather than other angle from the instrument thus simplifying the optic and making the device cost effective. Such arrangement would allow replacing only the telescope if the telescope is damaged or if it wears out rather than discarding the whole device.

OBJECT OF THE INVENTION

The object of the invention is to provide a motor drive assembly that is detachable from a handle assembly of an instrument and also detachable from a gear assembly of the instrument for the purpose of replacing a motor drive assembly with a new motor drive assembly when the motor drive assembly is damaged due to multiple uses.

Another object of the invention is to provide a detachable motor drive assembly from the handle assembly and the gear assembly for the purpose of reusing the motor drive assembly after cleaning and/or sterilizing and/or autoclaving it such that it is clean of all contaminants before use.

Yet another object of the invention is to enable cleaning and/or sterilizing and/or autoclaving the handle assembly and/or the gear assembly which can get contaminated by contaminants and/or blood and/or tissue due to multiple use and such that it can be reused.

Yet another object of the invention is that, if the handle assembly wears, then the handle assembly can be replaced with a new handle assembly.

Yet another object of the invention is to enable detachment of the blade or cutter tube from an outer tube of the instrument, replace either of them or both with a new one if it wears due to multiple uses.

Another object of the invention is to enable detachment of the cutter/blade tube from outer tube to clean and/or sterilize and/or autoclave the blade/cutter tube and/or outer tube so that it is clean of all contaminants and/or blood and/or tissue so that it can be reused after cleaning and/or sterilizing and/or autoclaving.

Another object of the invention is to provide a telescope which is in a straight alignment with the blade/cutter tube assembly and that can be detached from the instrument and replaced with a new one. Any standard telescope can be used as a replacement to older one. In case of damage or if the telescope wears out there is no need to replace complete device. It therefore allows replacement of only the telescope rather than discarding the whole device.

Yet another object of the invention is to provide the telescope which is in a straight alignment with the blade/cutter tube assembly that can also be cleaned and/or sterilized and/or autoclaved and reused so that it is clean of all contaminants and also provides a clear vision.

SUMMARY OF THE INVENTION

This invention discloses an instrument 1, which is a morcellator, particularly a urological morcellator with a motor drive assembly 2 that is detachable from a handle assembly 3 and detachable from a gear assembly 5 for the purpose of reusing or replacing the motor drive assembly.

Figure 06:
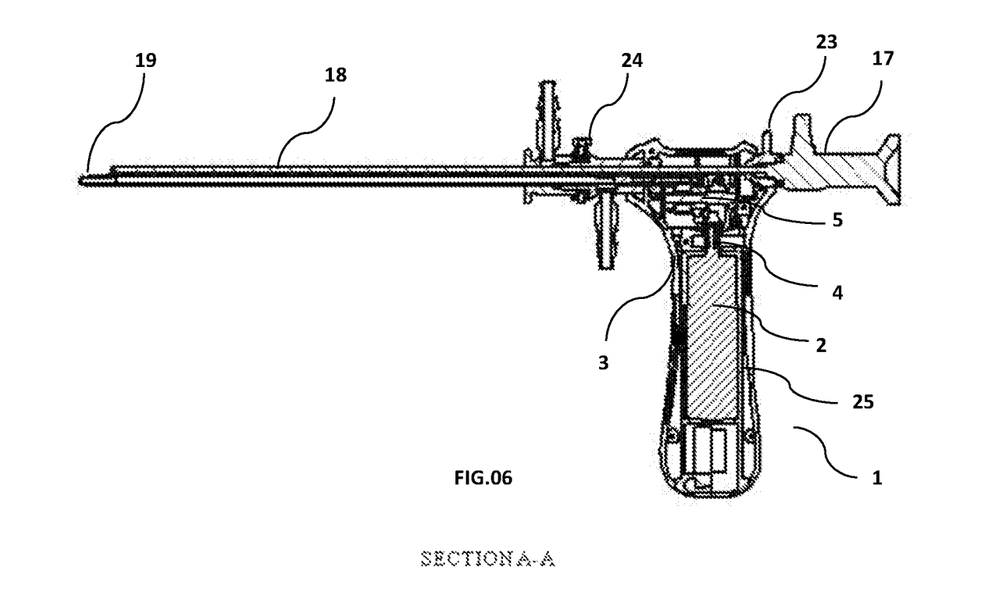
FIG. 6 illustrates the sectional view of the instrument along the line A-A displayed in FIG. 5.
Figure 07:
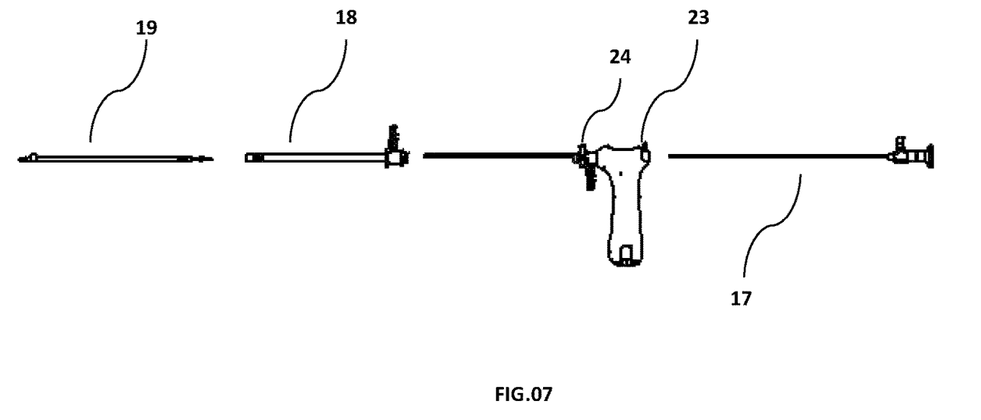
FIG. 7, illustrates a button when pressed the outer sheath can be detached which can be removed out completely.

As illustrated in FIG. 6 and FIG. 7 a telescope 17 is provided in a straight alignment to a cutter/blade tube assembly 19. When a button 23 is rotated the telescope 17 is detachable from the instrument. This telescope is in straight alignment to the cutter/blade tube assembly 19.

As shown in FIG. 7, when a button 24 is pressed an outer sheath 18 can be detached which can be removed out completely. The cutter/blade tube assembly 19 present inside the outer sheath 18 can be detached eventually.

This provides an advantage to detach the blade/cutter tube from the outer tube, replace both or either one with a new one if it wears due to multiple use or to detach the cutter/blade tube and outer tube, clean and/or sterilize and/or autoclave it so that it is clean of all contaminants and/or blood and/or tissue so that it can be reused after sterilizing and/or cleaning and/or autoclaving.

Figure 11:
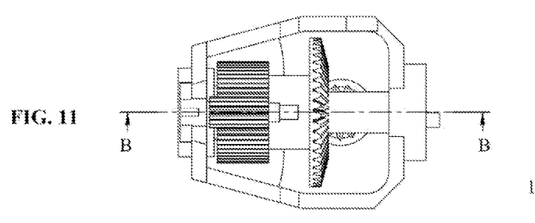
Figure 12:
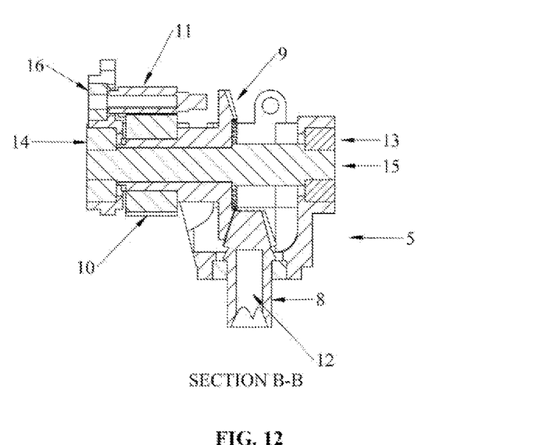
FIG. 12 illustrates a sectional view of the gear assembly along the line B-B shown in FIG. 11.

FIG. 12 illustrates a sectional view of the gear assembly 5 along the line B-B shown in FIG. 11 that is present inside a gear box casing 7 with internal parts comprising of an at least one first bevel gear 8 and an at least one second bevel gear 9, an at least one first spur/helical gear 10 and an at least one second spur/helical gear 11. Any combination of the gear can be used to achieve the motion.

The gear assembly 5 further comprises of an at least one first bearing-bush 13, an at least one second bearing/bush 14 in alignment with at least one first gear shaft 15. An at least one third bearing/bush 16 holds the second spur/helical gear 11. This motion can also be achieved by worm wheel mechanism.

DESCRIPTION OF THE INVENTION

Figure 01:
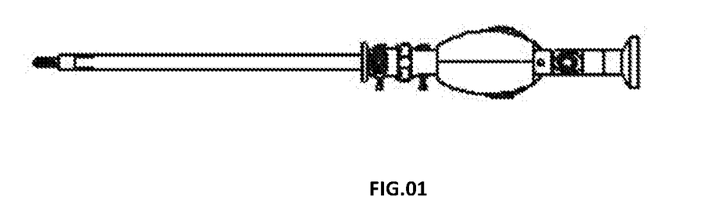
FIG. 1 illustrates the top view of the instrument.
Figure 02:
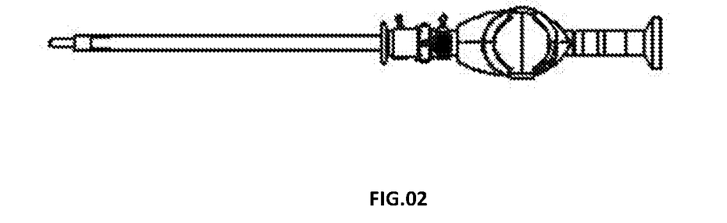
FIG. 2 illustrates the bottom view of the instrument.
Figure 03:
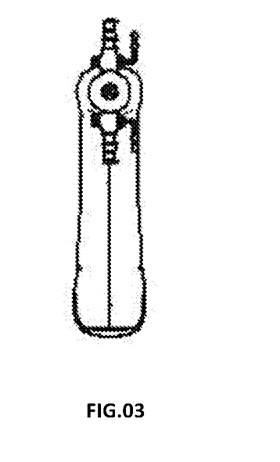
FIG. 3 illustrates the left hand view of the instrument.
Figure 04:
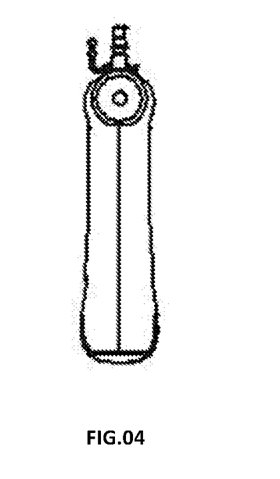
FIG. 4 illustrates the right hand view of the instrument.

FIG. 1 illustrates the top view of the instrument. FIG. 2 illustrates the bottom view of the instrument. FIG. 3 illustrates the left hand view of the instrument. FIG. 4 illustrates the right hand view of the instrument.

Figure 05:
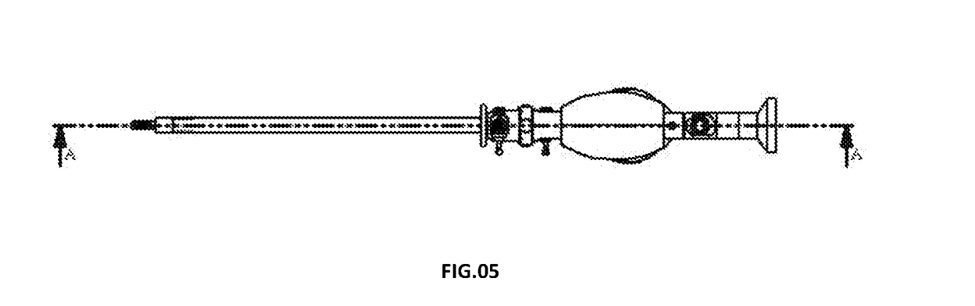

FIG. 6 illustrates the sectional view of the instrument along the line A-A displayed in FIG. 5.

As per FIG. 6, the invention discloses a medical instrument 1 which is a morcellator, particularly a urological morcellator, with a motor drive assembly 2 that is detachable from a handle assembly 3 and detachable from a gear assembly 5 for the purpose of reusing or replacing the motor drive assembly.

FIG. 6 illustrates a motor drive assembly 2 with an integrated square connector 4 inside a casing 25 of the instrument giving it mechanical advantage of direct drive leading to lesser mechanical loss. Wire cable can be used instead of gear mechanism.

The purpose of the invention is to provide a motor drive assembly that is detachable from the handle assembly and also detachable from the gear assembly for the purpose of replacing the motor drive assembly with a new motor drive assembly when the motor drive assembly damages due to multiple uses.

Another purpose of the invention is to provide a detachable motor drive assembly from the handle assembly and the gear assembly for the purpose of reusing the motor drive assembly after cleaning and/or sterilizing and/or autoclaving it such that it is clean of all contaminants before use.

As illustrated in FIG. 6 and FIG. 7, a telescope 17 is provided in straight alignment to a cutter/blade tube assembly 19 of the instrument. When a button 23 is rotated the telescope 17 is detachable from the instrument. This telescope is provided in straight alignment to the cutter/blade tube assembly 19.

In another embodiment, the telescope can be in any other angle to the instrument.

The present invention provides a telescope which is in a straight alignment with the cutter tube and that can be detached from the instrument and replaced with a new one. Any standard telescope can be used as a replacement to older one.

The telescope can also be cleaned and/or sterilized and/or autoclaved and reused so that it is clean of all contaminants and also provides a clear vision.

As shown in FIG. 7, when a button 24 is pressed an outer sheath 18 of the instrument can be detached which can be removed out completely. The cutter/blade tube assembly 19 present inside the outer sheath 18c an be detached eventually.

This provides the advantage to detach the blade/cutter tube from the outer tube, replace both or either one with a new one if it wears due to multiple use or to detach the cutter/blade tube and outer tube, clean and/or sterilize and/or autoclave it so that it is clean of all contaminants and/or blood and/or tissue so that it can be reused after sterilizing and/or cleaning and/or autoclaving.

Figure 08:
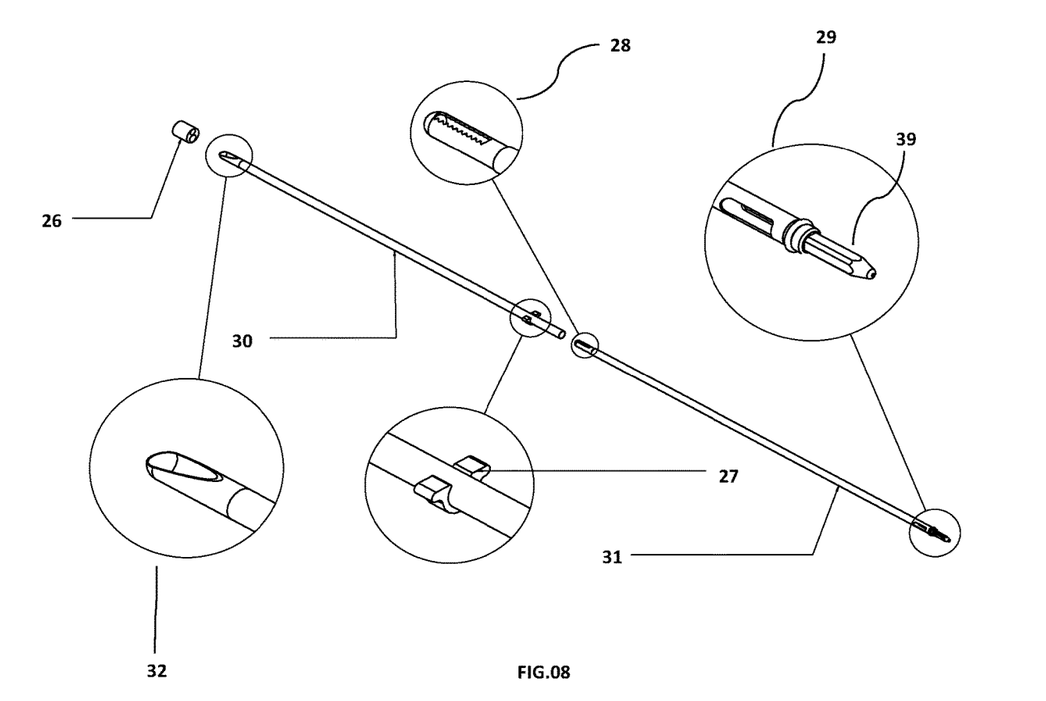
FIG. 8 illustrates cutter/blade tube inside the cutter/blade tube assembly.

FIG. 8 illustrates a cutter/blade tube 31 inside the cutter/blade tube assembly 19 where the cutter/blade tube 31 rotates inside the outer tube 30 and a tissue shears/cuts between sharp edge of cutter/blade part of the cutter/blade tube 31 and front concave part of an outer tube 30. There is an outer tube support 27. Front concave part of outer tube 30 is shown in detail view 32. Front cutter/blade part of inner cutter/blade tube 31 is shown in detail view 28. Back square part of inner cutter/blade tube 31 is shown in detail view 29. There is a front scope support 26.

Figure 09:
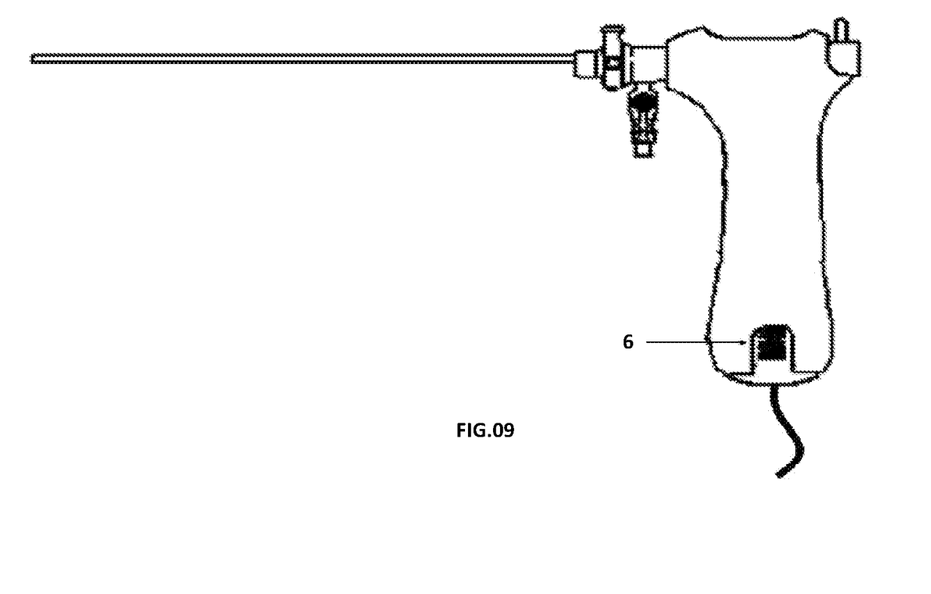
FIG. 9 illustrates button for detaching the motor drive assembly present inside the casing from the gear assembly and the handle assembly.

FIG. 9 illustrates a button 6 for detaching the motor drive assembly 2 present inside the casing 25 from the gear assembly 5 and the handle assembly 3 (as illustrated in FIG. 06).

The detachable motor drive assembly provides the advantage of replacing the old motor drive assembly with a new motor drive assembly when it gets damaged after multiple uses.

The motor drive assembly after detachment can be cleaned and/or sterilized and/or autoclaved such that it is clean of all the contaminants and can be reused.

The handle assembly and/or the gear assembly can be cleaned and/or sterilized and/or autoclaved and reused such that it is clear of contaminants and/or blood and/or tissue.

Figure 10:
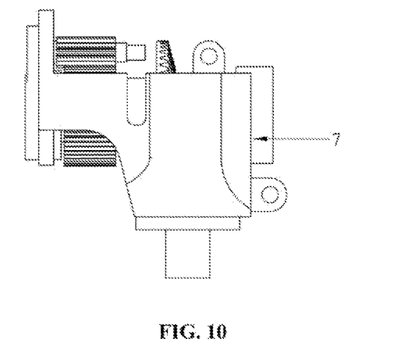
FIG. 10 illustrates a gear assembly inside a gear box casing.

FIG. 10 illustrates a gear assembly 5 inside a gear box casing 7.

FIG. 12 illustrates a sectional view of the gear assembly 5 along the line B-B shown in FIG. 11 that is present inside the gear box casing 7 with internal parts comprising of an at least one first bevel gear 8 and an at least one second bevel gear 9, an at least one first spur/helical gear 10 and an at least one second spur/helical gear 11. Any combination of the gear can be used to achieve the motion.

The gear assembly 5 further comprises of at least one first bearing/bush 13 and at least one second bearing/bush 14 in alignment with at least one first gear shaft 15. Further, at least one third bearing/bush 16 holds the second spur/helical gear 11. This motion can also be achieved by worm wheel mechanism.

There is at least one opening 12 in the first bevel gear 8 for integrated square connector 4 engagement. The opening 12 may be square or any other shape.

The integrated square connector 4 (shown in FIG. 6) is connected to an opening 12 in the first bevel gear 8 which can be detached by pressing button 6 to detach the motor drive assembly 2.

In an embodiment, the flexible shaft can be attached to rotate the cutter.

Figure 13:
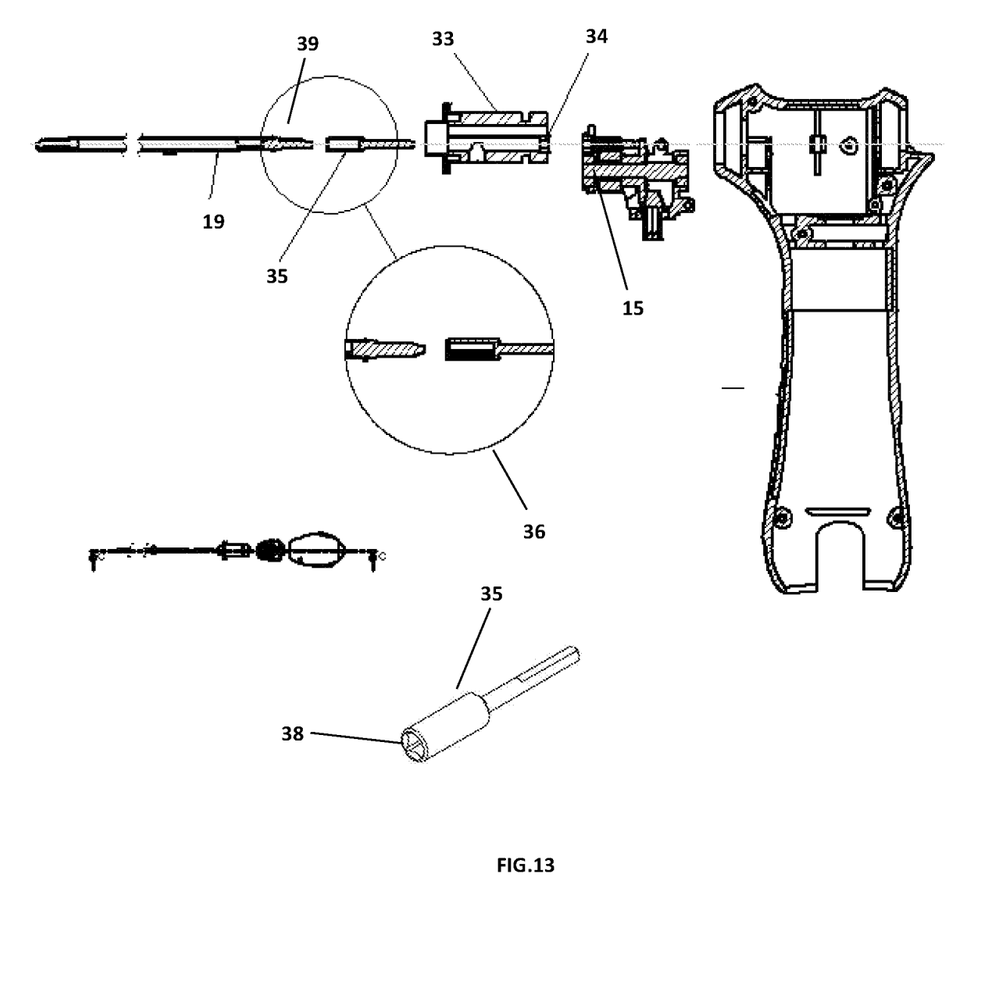
FIG. 13 illustrates exploded view of handle assembly with cutter/blade tube with at least one second gear shaft that connects with the at least one square connector of cutter/blade tube.

FIG. 13 illustrates an exploded view of handle assembly with cutter/blade tube with at least one second gear shaft 35. There is an outer sheath support 33. At least one square connector 39 of cutter/blade tube, shown in detail view 29 of FIG. 8 couples with an at least one square cavity 38 of second gear shaft 35. At least one fourth bearing 34 connects with the at least one second gear shaft 35 of assembly.

Figure 14:
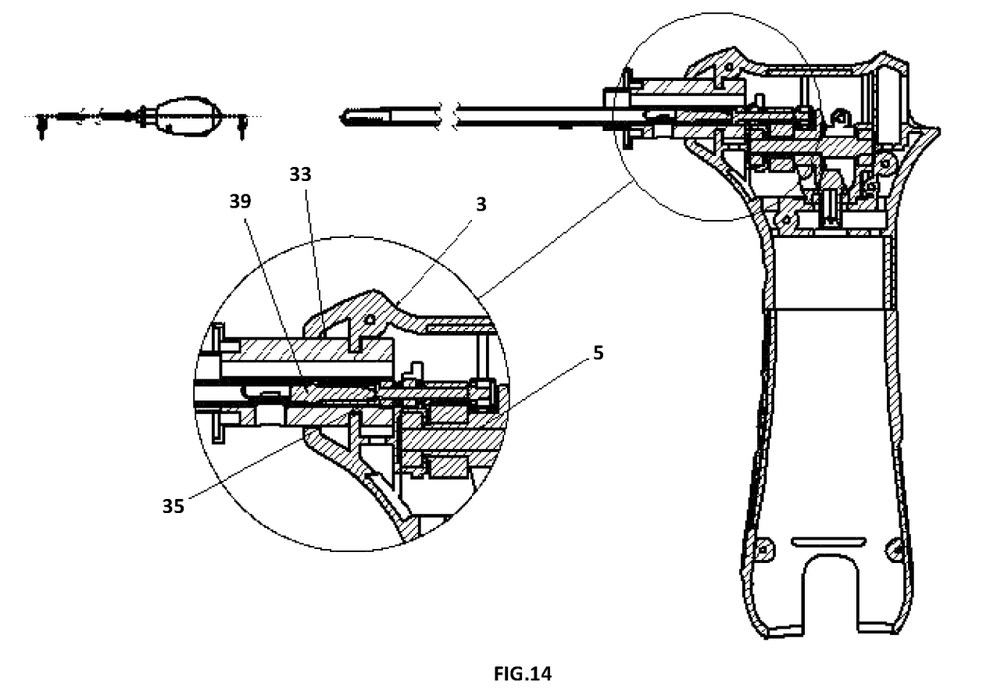
FIG. 14 illustrates the detail view of the gear assembly where the at least one square connector of the cutter/blade tube couples with at least one second gear shaft.

FIG. 14 illustrates the detail view of the gear assembly where the at least one square connector 39 of the cutter/blade tube couples with at least one second gear shaft 35 due to its square profile and positively engages with each other for rotational motion of the cutter/blade tube about its axis.

Figure 15:
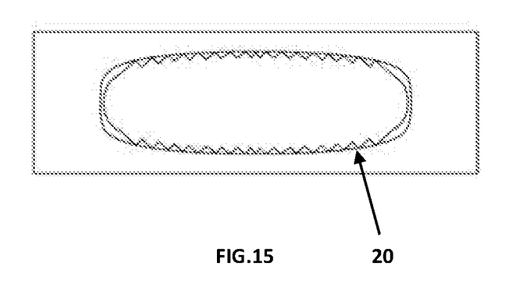
FIG. 15 illustrates a top view of the cutter/blade part of the cutter/blade tube displaying sharp teeth like projections 20 in the central oval region for cutting purpose of the tissue.

FIG. 15 illustrates a top view of the cutter/blade part of the cutter/blade tube displaying sharp teeth like projections 20 in the central oval region for cutting purpose of the tissue.

Figure 16:
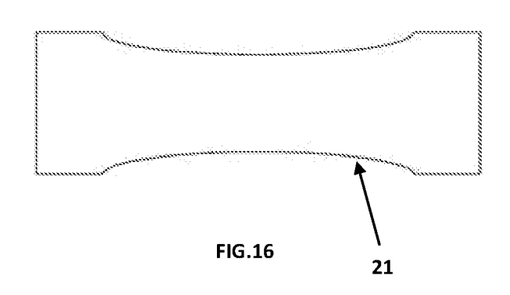
FIG. 16 illustrates a front view of the cutter/blade part of the cutter/blade tube displaying a concave region 21 on both top and bottom side.

FIG. 16 illustrates a front view of the cutter/blade part of the cutter/blade tube displaying a concave region 21 on both top and bottom side.

Figure 17:
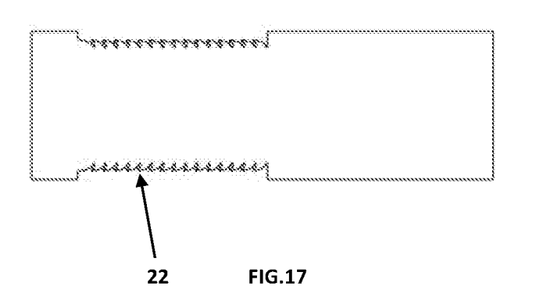
FIG. 17 illustrates a top view of another embodiment of the cutter/blade part of the cutter/blade tube displaying the sharp edges 22 at the sides.

FIG. 17 illustrates a top view of another embodiment of the cutter/blade part of the cutter/blade tube displaying the sharp edges 22 at the sides.

Figure 18:
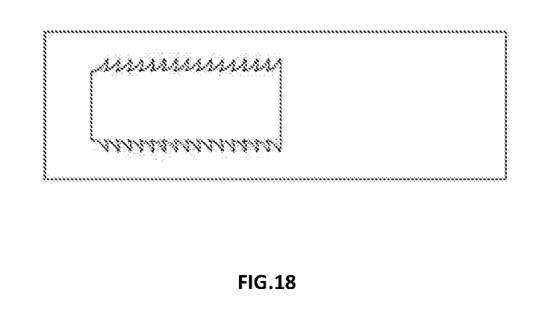
FIG. 18 illustrates a front view of FIG. 17 of the cutter/blade part with sharp edges on a rectangular area on the cutter part.

FIG. 18 illustrates a front view of FIG. 17 of the cutter/blade part with sharp edges on a rectangular area on the cutter part.

The instrument can be used without limitation in gynecological surgeries, laparoscopic surgeries, hysterectomy surgeries, benign prostatic hyperplasia (BPH) surgeries and other similar such surgeries.

I claim:

1. An instrument comprising a motor drive assembly that is detachable from a handle assembly and detachable from a gear assembly, wherein the gear assembly is positioned inside the handle assembly, and wherein the motor drive assembly is detachable for the purpose of being reused after cleaning or replacement, wherein the instrument further comprises:

a cutter/blade tube assembly, wherein the cutter/blade tube assembly comprises a cutter/blade tube and an outer tube, wherein the outer tube is detachable from the cutter/blade tube, and wherein an at least one square connector of the cutter/blade tube couples with an at least one square cavity of a second gear shaft due to a square profile of the at least one square connector, and the at least one square connector positively engages the at least one square cavity for enabling rotational motion of the cutter/blade tube about an axis of the cutter/blade tube; and a telescope in straight alignment to the cutter/blade tube assembly, said telescope, through actuation of a first button, being detachable for cleaning or being replaced with a new telescope.

2. The instrument as claimed in claim 1, wherein the instrument is an urological morcellator.

3. The instrument as claimed in claim 1, wherein the cutter/blade tube rotates inside the outer tube to shear/cut a tissue between a sharp edge of a cutter/blade part of the cutter/blade tube and a front concave part of the outer tube.

4. The instrument as claimed in claim 1, wherein the gear assembly further comprises any or a combination of a first bevel gear, a second bevel gear, a first spur/helical gear, a second spur/helical gear, a first bearing/bush, a second bearing/bush that is in alignment with a first gear shaft, and a third bearing/bush that holds the second spur/helical gear.

5. The instrument as claimed in claim 4, wherein there is at least one opening in the first bevel gear of the gear assembly inside the handle assembly for engagement with an integrated square connector.

6. The instrument as claimed in claim 1, wherein the motor drive assembly comprises an integrated square connector that is positioned inside a casing of the instrument.

7. The instrument as claimed in claim 1, wherein said instrument further comprises of a second button, which when pressed, enables detachment of an outer sheath completely to enable the cutter/blade tube assembly present inside the outer sheath to get detached.

\* \* \* \* \*